(12) United States Patent
Bernardini et al.

(10) Patent No.: US 9,596,845 B2
(45) Date of Patent: Mar. 21, 2017

(54) FORMULATIONS BASED ON 3-IODO-2-PROPYNYL BUTYL CARBAMATE

(75) Inventors: Marco Bernardini, Lodi (IT); Francesca Borgo, Milan (IT); Edoardo Russo, Piacenza (IT); Luigi Capuzzi, Novara (IT); Robert Alber, Prien (DE)

(73) Assignee: Sipcam S.P.A., Milan (IT)

( * ) Notice: Subject to any disclaimer, the term of this patent is extended or adjusted under 35 U.S.C. 154(b) by 625 days.

(21) Appl. No.: 13/448,165

(22) Filed: Apr. 16, 2012

(65) Prior Publication Data
US 2012/0207844 A1 Aug. 16, 2012

Related U.S. Application Data

(63) Continuation of application No. 12/067,450, filed as application No. PCT/EP2006/008953 on Sep. 14, 2006, now abandoned.

(51) Int. Cl.
*A01N 25/28* (2006.01)
*A01N 47/12* (2006.01)

(52) U.S. Cl.
CPC ............. *A01N 25/28* (2013.01); *A01N 47/12* (2013.01)

(58) Field of Classification Search
None
See application file for complete search history.

(56) References Cited

U.S. PATENT DOCUMENTS

| 6,641,827 B2 * | 11/2003 | Yoshida ................ A01N 65/00 424/405 |
| 6,946,427 B2 * | 9/2005 | Lutz et al. .................... 504/140 |
| 7,229,949 B2 | 6/2007 | Jadhav et al. |
| 7,781,498 B2 | 8/2010 | Krishnan |
| 2006/0009519 A1 * | 1/2006 | Matsuo .................... B27K 3/38 514/543 |
| 2006/0063001 A1 * | 3/2006 | Hart ....................... A01N 43/80 428/402.2 |
| 2007/0196410 A1 * | 8/2007 | Jadhav et al. ................ 424/408 |

OTHER PUBLICATIONS

Ibrahim et al.—abstract # 114:25832 HCAPLUS of Pertanika (1989) 12 (3) pp. 409-412 Performance of Microencapsulated Fungicide.

* cited by examiner

*Primary Examiner* — Robert A Wax
*Assistant Examiner* — Melissa Mercier
(74) *Attorney, Agent, or Firm* — Arent Fox LLP

(57) ABSTRACT

Formulations in water suspension of microcapsules based on 3-iodo-2-propynyl butyl carbamate (IPBC) comprising (parts by weight): (a) 10-60 parts of polymeric microcapsules comprising inside them IPBC and a synergizing agent formed of one or more alkylbenzenes having a number of carbon atoms from 9 to 20; (2) 1-5 parts of one or more dispersants; (3) 1-20 parts of one or more excipients selected from thickeners, antifoam, antifreeze, in can preservative agents; (4) water to 100.

15 Claims, No Drawings

FORMULATIONS BASED ON 3-IODO-2-PROPYNYL BUTYL CARBAMATE

CROSS-REFERENCE TO RELATED APPLICATION

This is a Continuation Application of U.S. patent application Ser. No. 12/067,450, filed Mar. 19, 2008; which is a National Stage entry of International Application No. PCT/EP2006/008953, having an international filing date of Sep. 14, 2006; which claims priority to Italian Application No. MI2005 A 001724, filed Sep. 19, 2005. The disclosures of these prior applications are hereby incorporated herein its entirety by reference.

The present invention relates to stable water formulations of 3-iodo-2-propynyl butyl carbamate (IPBC) and to its preparation process.

More specifically the present invention relates to water suspensions of microcapsules containing IPBC having the following combination of properties:

- high chemical stability to UV and storage for long periods, even of one year;
- high physical stability, in particular with reference to the absence of irreversible sedimentation;
- substantial maintenance of the colour of the formulation, even after long storages;
- release of the active (biocide) through the microcapsule so that the microencapsulated agent develops biocidal activity;
- release tuning in function of the application;
- high efficacy of the biocidal activity in the time;
- low toxicity and improved environmental compatibility.

The compound 3-iodo-2-propynyl butyl carbamate (IPBC) is a crystalline solid largely used as wide action spectrum biocide. In particular IPBC is used to preseve from the fungus attack various types of substrata, intermediate compositions and final product, as for example paints and other coating products, surfactants, proteins, starch-based compositions, products for cosmetic use, inks, emulsions, resins, plasters, cement surfaces, wood, skins, plastics and textiles, lubricants and working fluids used in industrial circuits.

The use of said biocide is widely known to prevent degradation due to the microorganism action also in polymeric dispersions, water based products, latexes containing polyvinyl alcohol, polyacrylates or vinyl polymers, thickening solutions containing cellulose derivatives, kaolin-based suspensions. Said degradation in fact can negatively impart the quality and the performances of these products as the microorganism attack produces, among other effects, variations in the pH and in the rheological properties of the compositions, decoloration, gas formation and smells.

Even the same IPBC is subjected to degradation on various grounds, as for example the variation of pH, the high temperatures, but above all for the presence of UV rays which trigger photooxidation reactions. The degradation is practically shown by the formation of elementary iodine and other free radicals which, besides decreasing the biocidal efficacy thereof, confer to the IPBC-based compositions and, consequently to the substratum on which said compositions are applied, a coloration ranging from yellow to brown. The yellowing is particularly a drawback in substrata where a white colour is desired. The IPBC degradation is observed in water-based formulations and also in IPBC solvent-based formulations as, for example, N-methyl pyrrolidone, Texanol® (2,2,4-trimethyl-1,3-pentandiolisobutyrate), dimethylsulphoxide (DMSO) and dipropylene glycol. For the former, where the active is dispersed by suitable coformulants, there is also the further drawback due to the IPBC strong tendency to crystallize in water causing in the time sedimentation and mass thickenings. These phenomena make therefore unstable the IPBC containing compositions.

Numerous IPBC liquid biocide formulations are known in the prior art additioned with suitable compounds to improve the IPBC chemical stability. For example, U.S. Pat. No. 4,552,885 describes the use of 2,2,6,6-tetraalkylpiperidine and of a UV absorber to stabilize fungicide organic liquid formulations of for example IPBC, against the degradation caused by the light.

U.S. Pat. No. 4,276,211 describes an epoxidated organic stabilizer to be added to liquid compositions containing iodo alkynyl carbamates, as IPBC, to reduce the yellowing phenomenon.

U.S. Pat. No. 6,353,021 describes biocidal liquid compositions containing halopropynyl butyl carbamate, such as IPBC, stabilized to the degradation and the yellowing by using a synergistic mixture of a UV absorber and an epoxidated organic component.

U.S. Pat. No. 6,616,740 describes IPBC liquid compositions in solvent, for example Texanol®, additioned with polyethylen glycol, or with polypropylen glycol or with polypropylen glycol glyceryl ester, showing colour stability, even at high tempertures and at the light.

U.S. Pat. No. 6,506,794 describes water IPBC formulations stabilized by the use of partially hydrolyzed polyvinyl alcohol and a wetting agent.

U.S. Pat. No. 5,827,522 describes formulations based on IPBC and alkoxylated or hydrogenated castor oil, or an alkoxylated resin oil (rosin), capable to form stable microemulsions for some months once diluted in water. These IPBC liquid biocidal formulations show the following drawbacks: when the solvent of the biocidal formulations is immiscible with water, the IPBC formulations are incompatible, that is, immiscible, with aqueous compositions causing unhomogeneous end compositions. When, on the contrary, the solvent is miscible with water, besides dissolving in waste waters and penetrating the ground, it is not capable to solubilize IPBC which immediately crystallizes bringing to a decrease of its efficacy.

Water IPBC biocidal formulations in the form of IPBC dispersions show drawbacks. When stored for long periods they partially loose their biocidal efficacy owing to the tendency of the IPBC crystals to grow during the time.

Compositions wherein the biocide is encapsulated in order to have an improved environmental compatibility with respect to the above mentioned solvent or water biocidal formulations are also known.

For example U.S. Pat. No. 6,365,066 describes compositions having an antidirtying action formed of filming and biocidal agents, for example those belonging to the iodo-derivative class, wherein the biocide is coated by a polymeric material and is in microcapsule form. However IPBC microcapsules are not described and the IPBC chemical and physical stability in microcapsules is not disclosed, in particular the release. Furthermore no indication is given on the fact that IPBC can be released, preferably in a controlled way.

Patent application US 2004/0234603 describes plasters of various biocides having highly basic pH containing micro capsules and showing a high stability in basic environment. Tests on the biocide degradation are given when the plaster is subjected to a thermal treatment, for example at 54° C. IPBC in microcapsules formed of formaldehyde-melamine is described, but neither examples are given on the fact that IPBC is really released from the microcapsules, nor any indication on its controlled release. The biocidal activity, in particular fungicidal, of the microcapsules, implicitly showing the release of the active principle, is described only for another biocide, the pyirithione zinc. It has to be observed that an essential feature of the microincapsulated biocides is to allow the release of the encapsulated biocide during in the time. This characteristic is not predictable a priori. Another drawback of the microencapsulated biocide exemplified in the above patent application is that the resin used for the IPBC microencapsulation is formaldehyde-melamine, whose environmental problems due to the presence of traces of formaldehyde are known. From what reported in the above application one cannot decide whether the IPBC-based microcapsules are effective or not in the biocidal activity: it is indeed essential that the biocidal products contained in the capsule are released in the time. This patent neither gives any indication about the release, nor about the possibility to control the release during the time.

The abstract of the Thai publication "Preparation of microincapsulated fungicide used in paint", 1998, describes IPBC in ureaformaldehyde microcapsules. However these microcapsules are prepared with a process having an encapsulation efficency of 63.46%. This does not make acceptable the microencapsulated biocides obtained in this way as the IPBC is a very expensive product. Besides, the combination of the above properties is not even mentioned.

The need was felt to have available IPBC compositions showing the following combination of properties:
  high chemical stability to UV and storage for long periods, even of one year;
  high physical stability, in particular with reference to the absence of irreversible sedimentation;
  substantial maintenance of the colour of the formulation and absence of yellowing phenomena, even after long storages;
  release of the active (biocide) through the microcapsule so that the microencapsulated agent develops biocidal activity;
  release tuning in function of the application;
  high efficacy of the biocidal activity in the time;
  low toxicity and improved environmental compatibility;
  water-based to be used also in water environments;
  obtainable by a simple and high efficiency encapsulation process, preferably higher than 90%, more preferably higher than 94%.

The Applicant has surprisingly and unexpectedly found a specific formulation comprising IPBC showing the combination of the above properties.

An object of the present invention are formulations in aqueous suspension of microcapsules based on 3-iodo-2-propynyl butyl carbamate (IPBC) comprising the following components (parts by weight):
(1) 10-60 parts of polymeric microcapsules comprising in the microcapsules IPBC and a synergizing agent formed of one or more alkylbenzenes, linear or branched, having a number of carbon atoms from 9 to 20, preferably from 10 to 16;
(2) 1-5 parts of one or more dispersants;
(3) 1-20 parts of one or more excipients selected from thickeners, antifoam, antifreeze, antimould agents;
(4) water to 100.

The ratio by weight IPBC/alkylbenzenes ranges between 1:0.5 and 1:2, preferably between 1:1 and 1:1.5

The microcapsules of the present invention are usually dispersed in water and have sizes 1-30 micron, preferably from 2 to 20 micron. The microcapsules comprise a reservoir of biocidal active in admixture with a suitable coformulating agent (synergizing agent), as above, and an external wall. The wall is formed by a polymeric membrane insoluble in water obtained by in situ interfacial polymerization. The polymers are those obtained by polycondensation, preferably not using formaldehyde as comonomer. Polyamides, polyesters, polyvinyl-alcohols, polyurethanes, polyurea, polylactic acid, more preferalbly polyurea, can for example be mentioned.

The IPBC of component (1) is generally available under the form of white crystalline solide and has generally a purity of 98%.

The synergizing agent of component (1) has a boiling point generally in the range 165° C.-310° C. Preferably it has a distillation range in the range 160°-180° C., or in the range 220°-290° C. It is generally available as Solvesso® 150, Solvesso® 200, Solvesso® 150 ND, Solvesso® 200 ND, preferably in the grades naphthalene residue free such as Solvesso® 150 ND, Solvesso® 200 ND. The synergizing agent formed by a mixture of alkylbenzenes having a distillation range in the range 182°-202° C. or in the range 226°-284° C. is preferred.

In alternative, as synergizing agent, it is possible to use biphenyl compounds such as diisopropyl biphenyl isomers mixture ($C_{18}H_{22}$).

The dispersant (component (2)) is generally selected among sodium ligninsulphonates, for example Reax® 100M, and calcium ligninsulphonates, for example Borrement® CA, etO-propO block polymers (block polymers containing ethylenoxide and propylenoxide blocks), for example Pluronic® 10400, sodium polycarboxylates, for example Geropon® TA 72, polyalkenyl pyrrolidone, for example Agrimer® AL 10; preferably white solid dispersants are used in the applications where this is required.

Among the excipients (component (3)), as thickeners xanthan rubber can be mentioned, for example Rhodopol®; as antifoam silicone compounds can be mentioned; as antifreeze inorganic salts, for example calcium nitrate, sodium carbonate can be mentioned; as in can preservative substituted triazines and benzoisothiazolinones can be mentioned.

As said, the formulation of the present invention is formed of a suspension of microcapsules dispersed in a water phase and appears having a lactescent appearance.

The formulations of the present invention show the combination of the above properties. In particular the formulations are particularly advantageous for applications in aqueous environment as they do not cause the crystalline growth of the active. They are chemically and physically stable to UV and to high temperatures, without showing yellowing and crystalline growth phenomena for more than one year when stored at room temperature.

The Applicant has furthermore unexpectedly and surprisingly found that the use of the particular synergizing agent of the invention in the IPBC microcapsules allows the biocide output through the polymeric walls without any break and obtaining a controlled IPBC release. The release is not a function of the temperature conditions and pH.

Without being bound to any theory, the Applicant deems that the controlled IPBC release takes place thanks to the fact that the particular coformulating agent of the present ivnention substantially inhibits the formation and the uncontrolled growth of IPBC crystals inside the microcapsule, thus avoiding the break of the microcapsule polymeric walls.

Besides it has been found that the synergizing agent is essential to obtain the microcapsules when polyurea is used as polymer of the wall of the microcapsules (see the comparative Examples).

For the above reasons the coformulating agent of the present invention can be defined as an IPBC synergizing agent. The controlled IPBC release is advantageous as it allows to maintain a high biocidal efficacy in the time.

The aqueous formulation of the present invention can be used as such or diluted before the use. Further it is possible to separate the microcapsules from the water formulations and use them as solid additives. Known separation techniques, can be used for example centrifugation, sedimentation, filtration, spray drying.

The formulations comprising the microcapsules of the present invention are obtainable, for example, according to the following process:

a) preparation of a homogeneous IPBC mixture and one or more alkylbenzenes, at a temperature generally in the range of about 15° C. and 70° C., preferably between 40° C. and 60° C.; the ratio by weight IPBC/alkylbenzenes ranges between 1:0.5 and 1:2, preferably between 1:1 and 1:1.5;

b) addition to the mixture obtained in a) of one or more water insoluble monomers, precursors of the polymer forming the microcapsule walls in amounts in the range 5-20% by weight, preferably 6-12% by weight with respect to the weight of the mixture obtained in a);

c) addition of the organic phase obtained in b) to an aqueous phase comprising at least one dispersant, in a ratio by weight aqueous phase/organic phase between 0.4:1 and 1:1, preferably between 0.6:1 and 0.9:1, thus obtaining an oil/water emulsion;

d) optional addition to the emulsion obtained in c) of the water-soluble monomers, precursors of the polymer forming the microcapsule walls in molar ratio 0.9-1, preferably 0.92-0.99, with respect to the monomers used in b);

e) heating at temperature in the range 50° C.-80° C., preferably 55° C.-70° C., to allow the formation of the polymeric membrane forming the microcapsule walls. In step d) and e) the in situ polymerization takes place.

In step a) homogeneous mixtures mean that there are no substantial phase separations. Preferably the homogenization is carried out under stirring.

Preferably step b) is carried out under stirring maintaining substantially the same temperature of step a). Examples of water-insoluble monomers are polymethylene polyphenyl isocyanate (MDI) or MDI mixtures with toluene diisocyanate (TDI), when the polymer of the microencapsulated biocide is polyurea or polyurethane. The isocyanate monomer is preferably Voronate® M220 (polymethylene polyphenyl isocyanate).

Step c) preferably takes place under strong stirring, more preferably by using a high "shear rate" stirrer having a speed higher than 5,000 rpm, for example of the Turrax type, for at least 3 minutes.

Step d) preferably takes place under stirring, more preferably by using a low "shear rate" stirrer, for example, of the blade type having a speed lower than 1,000 rpm.

As water soluble monomers to be used in step d) hexamethylendiamine, optionally in water solution, can be mentioned, in case of polyurea microcapsules.

Step d) is preferably used when only MDI is used to prepare the polyurea membrane.

When MDI is used in admixture with TDI, preferably step d) is not used.

The biocide release rate can be tuned by using or not step d) (see the Examples).

The formulations of the invention can comprise polyurea microcapsules obtained by using step d) and microcapsules obtained without using step d).

Step e) generally lasts for about 3 hours, or more.

The excipients (component 3)) can be added before or after step e).

Another object of the present invention is the process for preparing the formulations comprising the microcapsules of the present invention, as above described.

In particular, when the polymer forming the membrane is polyurea, the process preferably comprises the following steps:

a) preparation of a homogeneous IPBC mixture and one or more alkylbenzenes as above, under stirring, at a temperature in the range 25° C.-70° C., preferably 40° C.-60° C.; the ratio by weight IPBC/alkylbenzenes ranges between 1:0.5 and 1:2, preferably between 1:1 and 1:1.5, maintaining under stirring until complete homogenization;

b) addition to the mixture obtained in a) of a water-insoluble monomer, precursor of the polyurea polymer, preferably polymethylene polyphenyl isocyanate (MDI) or MDI mixtures with toluene diisocyanate (TDI), in amounts in the range 6-12% by weight with respect to the total weight of the mixture obtained in a), under stirring, maintaining substantially the same temperature of step a);

c) addition to an aqueous phase comprising at least one dispersant of the organic phase obtained in b), in a ratio by weight aqueous phase/organic phase between 0.6:1 and 0.9:1, under strong stirring, preferably by using a high "shear rate" stirrer, preferably having a speed higher than 5,000 rpm, more preferably of the Turrax type, for at least 3 minutes, thus obtaining an oil/water emulsion;

d) optional addition to the emulsion obtained in c) of a water-soluble monomer, precursor of the polyurea, preferably hexamethylendiamine, optionally in aqueous solution, in a molar ratio 0.9-1, preferably 0.92-0.99 with respect to the isocyanate used in b), under stirring, preferably by using a low "shear rate" stirrer of the blade type, more preferably having a speed lower than 1,000 rpm.

e) completion of the polymerization reaction by maintaining the temperature in the range 50° C.-80° C., preferably 55° C.-60° C., for at least three hours.

The in situ polymerization can takes place at atmospheric pressure. By using the in situ polymerization there is the advantage to obtain microcapsules having a variable porosity depending on the duration of the step e). Furthermore a variable thickness depending on the used monomers and on the particle size of the starting emulsion is obtained.

The thinner and the more porous of the walls allow indeed a faster release of the active in the substratum. Thicker walls have the active inside the capsule for a longer time and therefore there is a slow release.

As said above, a way to obtain a faster or slower release in the time is to use different starting monomers (see the Examples and steps d) and e)).

The process of the present invention shows the advantage to obtain high encapsulation efficiency of the active IPBC, generally higher than 94%, preferably 99%, more preferably 100%. This is defined as the amount of encapsulated IPBC with respect to the initial IPBC. The Applicant has indeed surprisingly and unexpectedly found that, by using the particular coformulating agent of the present invention it is possible to achieve the above high encapsulation efficiency. Tests carried out by the Applicant have shown that, by using other coformulating agent as those of the invention and capable to dissolve IPBC, for example DBE® (a mixture of 55-65% by weight dimethyl glutarate, 15-25% dimethylsuccinate, 10-25% dimethyladipate), the encapsulation efficiency is very low or negligible. The same happens when IPBC is used without any coformulating agents (see the comparative Examples).

As said, the formulations object of the present invention show several advantages for the operator safety. They are not flammable, they are less irritating and toxic, in particular by inhalation, with respect to the prior art compositions. This is particular important for the use of the formulates on woods, paints, plasters, cosmetics, lubricants and industrial fluids.

The formulations of the invention show several advantages from the environmental point of view, for example a low VOC. Furthermore the microcapsules do not cause any substantial percolation.

A further advantage is due to the stability of the formulation and to the controlled release. This reduces the number of applications on the substrata and therefore the cost.

As said, the biocidal formulations of the present invention can be used as such, or as solvent-based or water-based formulations, preferably water compositions.

The formulations and microcapsules of the present invention can be used as biocides for substrata, for paints, for coating products, for surfactants, for proteins, for starch-based compositions, for products for cosmetic use, for inks, for emulsions, for resins, for plasters, for cement surfaces, for wood, for leathers, for plastics, for textiles, for lubricants, for metal working fluids, for polymeric dispersions, for aqueous-based products, for latexes containing polyvinyl alcohol, for polyacrylates or vinyl polymers, for thickening solutions containing cellulose derivatives, for kaolin-based suspensions, etc. and in general when there is the problem of degradation due to the microorganism.

In addition it is possible to decrease the slow release rate of IPBC by using a particular compound inside the IPBC microcapsules together with the other components.

The Applicant has indeed unexpectedly and surprisingly found that the use of the synergizing agent as above described in presence of a particular compound belonging to the class of N-alkyl pyrrolidone inside the IPBC microcapsules allows to improve the control of IPBC release through the polymeric walls, in particular a slower IPBC release is obtained.

The Applicant has indeed found that the release of IPBC through the microcapsules can be reduced, for at least 40%, when N-alkyl pyrrolidone is present in combination with the synergizing agent inside the IPBC microcapsules.

It is thus a further object of the present invention formulations in aqueous suspension of microcapsules and microcapsules as above defined wherein the microcapsules comprise inside them a N-alkyl pyrrolidone wherein the alkyl substituent, is a $C_1$-$C_{18}$ alkyl, linear or branched, preferably $C_6$-$C_{16}$, in addition to the IPBC and the synergizing agent.

The N-akyl pyrrolidone is used in such amounts to comply with the following condition
the ratio by weight between IPBC and the mixture of N-alkyl pyrrolidone with the synergizing agent ranges between 1:1 and 1:2 provided that the synergizing agent is at least 50% by weight with respect to the total weight of the mixture of N-alkyl pyrrolidone with synergizing agent.

The microcapsules comprising the N-alkyl pyrrolidone can be obtained in the same way as described above by preparing the homogeneous mixture of IPBC with one or more alkylbenzenes as in step a) but in the presence of a N-alkyl pyrrolidone.

Depending on the amount of N-alkyl pyrrolidone, it is also possible to reduce the typical odour of alkybenzene compounds like Solvesso while controlling the release of IPBC.

Some illustrative but not limitative Examples of the present invention follow.

EXAMPLES

Characterization
Content of Active Principle (Biocide)
It is determined by gaschromatography by using a FID (Flame Ionization Detector) type detector and a solution at 0.4% of dipropylphthalate in acetone as internal reference and acetone as solvent capable to dissolve the capsules and IPBC.
Granulometry of the Microcapsules
The distribution of the microcapsule sizes is measured by an infrared ray Malvern Mastersizer.
Viscosity of the Microcapsule Suspension
It is measured by using a LVT model Brookfield viscometer.
Stability to the Dilution
The stability to the dilution is evaluated by suspendability measurements determined by the official method Cipac MT 161: the greater the suspensivity and the greater the composition stability.
Test of Accelerated Suspension Stability
This test is used to evaluate the behaviour of the suspensions at room temperature for times over one year, by assuming that one day at 54° C. correspnds to at least 1 month at room temperature.

According to the standard test CIPAC MT 46, after the formulation residence for 14 days at 54° C. (ageing test) the formulation characteristics: titre, colour, encapsulation efficiency are again evaluated.
Colour Stability
The evaluation of the suspension colour change is visually carried out before and after the ageing test.
Efficiency of Encapsulation and IPBC Release
The encapsulation efficiency and the IPBC release are evaluated by maintaining the formulation in contact with hexane, a solvent capable to solubilize the free IPBC (not encapsulated) in the supension, but not capable to dissolve the polyurea polymer of the microcapsules. The per cent IPBC amount extracted is gaschromatographically determined in correpondence of precise time intervals: 1', 5', 15', 30', 60'.

The IPBC amount after 1 minute allows to evaluate the minimum encapsulation efficiency. From the trend of the subsequent data at 1 minute it is possible to evaluate the IPBC release rate from the capsules.

Values at 1' and at 60' are herein reported.
Test for the Evaluation of IPBC Release in Water
In order to simulate the behaviour of the product in real conditions, a test for the evaluation of IPBC release in water has been performed in the way here described.

0,4 g of formulated product corresponding to 20% of IPBC are dispersed in 1 litre of distilled water and maintained under magnetic stirring (300 rpm) for the lime necessary to perform the test.

10 ml samples are collected at fixed times (15 min, 30 min, 60 min, 2 hours, 4 hours and 7 hours) and filtered on a 45 micron filter.

The samples thus obtained are analysed by HPLC and IPBC content, corresponding to the fraction released through the capsules, is determined.

Example 1

To 250 g of Solvesso® 200 (mixture of $C_9$-$C_{16}$ alkylbenzenes having a distillation range in the range 226°-284° C.) contained in a vessel equipped with stirrer, 204 g of IPBC having a 98% purity are added; the mixture is heated to 50° C., maintaining under stirring until complete homogenization. Then, always under stirring, 31.8 g of Voronate® M 220 (isocyanate MDI) are added.

In the meantime 5 g of dispersant Agrimer® AL 10 are dispersed in 336 g of water and the above prepared organic mixture is added thereto, by stirring by Turrax at the maximum rate, equal to 10,000 rpm, for about 3 minutes, obtaining an oil/water emulsion.

Then, always under stirring by a blade stirrer at 800 rpm, 30.6 g of an aqueous solution containing 40% by weight of hexamethylene diamine are added.

The so obtained mixture is transferred into a reactor maintained at 50° C. After few minutes the formulation is completed by addition of 41 g of thickening agent (Rhodopol® 23 pregelified at 2.7% by weight in water and containing 1 g of Proxel® GXL as antimould agent), 2 g of antifoam agent Defomex® 1510 and allowed to mature for four hours at 60° C.

At the end of the 4 hours 80 g of calcium nitrate are aded and, after cooling at room temperature, 20 g of Geropon® TA 72 (sodium polycarboxylate) are added.

A suspension of microcapsules is obtained which is then subjected to the above charaterization obtaining the following results:

| IPBC content in the formulation: | | 20.1% |
|---|---|---|
| Granulometry: | 50% | <5 micron |
| | 90% | <20 micron |
| Viscosity: | | 1,700 cPs |
| Stability to dilution: | | suspendability 80% |

Furthermore the accelerated stability test of the microcapsule suspension has been carried out as described in the characterization, obtaining an IPBC content in the formulation of 19.4% and not observing any yellowing phenomenon.

The minimum variation of IPBC content, in combination with the maintenance of the values of the other characteristics, colour comprised, shows that the microcapsule suspension object of the present invention has substantially maintained unaltered its own starting characteristics, thus resulting stable in the time.

The above mentioned tests are indicative that the so prepared microcapsule suspension is preservable under the environmental conditions for long periods as sediments, mass thickenings, even under tropical conditions (T=54° C.) are not observed.

It was furthermore observed that, even after exposure for 30 days to light, the microcapsules are white and no yellowing phenomena are observed.

The release test carried out on the suspension before ageing has given the following values:

| Release at 1': | 1.1% |
|---|---|
| Release at 60': | 10.8% |
| Encapsulation efficiency: | >94% |

These data confirm that the microcapsule wall allows the IPBC outflowing in the time.

After suspension ageing the release test was repeated, obtaining release values substantially unchanged:

| Release at 1': | 1.1% |
|---|---|
| Release at 60': | 9.6% |

In order to evaluate the release of IPBC from microcapsules in aqueuos medium, and thus to simulate the behaviour of the product in real conditions, the test for IPBC release in water has been performed thus giving the following values:

| 15 min. | 50% |
|---|---|
| 30 min. | 53% |
| 60 min. | 62% |
| 2 h | 70% |
| 4 h | 80% |
| 8 h | 95% |

Example 2 (Comparative)

The same procedure of the Example 1 was repeated, except that IPBC was completely dissolved in DBE® instead of in Solvesso® 200.

At the time of the hexamethylendiamine addition it was noticed a significant thickening of the mass without capsule formation.

This shows that said solvent is not compatible with the formulation to be encapsulated.

Even by operating in an alternative way, that is, by using MDI in adnmixture with TDI without hexamethylendiamine, microcapsules are not obtained.

Example 3 (Comparative)

The same procedure of the Example 1 was repeated, except that no solvent was used in step a) and IPBC was liquefied at T=75° C. before proceeding with the polymerization process.

At the time of the aqueous phase addition to the organic phase formed of IPBC and MDI it was noticed an immediate crystallization of the active principle being it impossible to further proceed in the encapsulation.

This is an evidence of the need to operate in the presence of the particular coformulating agent of the present invention to obtain IPBC in polyurea microcapsules.

Example 4

By using the same procedure and equipment of the Example 1, to 250 g of Solvesso® 200, 204 g of IPBC having a 98% purity are added; the mixture is heated to 50° C., maintaining under stirring until complete homogenization.

Then 33.6 g of Voronate® M 220 (isocyanate MDI) and 16.8 g of toluene diisocyanate (TDI) are added.

In the meantime 5 g of dispersant Agrimer® AL 10 are dispersed in 428 g of water and the above prepared organic mixture is added thereto under stirring, obtaining an oil/water emulsion.

The so obtained mixture is transferred into a reactor maintained at 50° C. After few minutes the formulation is completed by addition of 41 g of thickening agent (Rhodopol® 23 pregelified at 2.7% by weight in water and containing 1 g of Proxel® GXL as antimould agent), 2 g of antifoam agent Defomex® 1510 and allowed to mature for four hours at 60° C.

At the end of the 4 hours and after cooling at room temperture 20 g of Geropon® TA 72 (sodium polycarboxylate) are added.

A suspension of microcapsules is obtained which is then subjected to the above charaterization obtaining the following results:

| IPBC content in the formulation: | 20% |
|---|---|
| Granulometry: | |
| 50% | <5 micron |
| 90% | <20 micron |
| Viscosity: | 1,750 cPs |
| Stability to dilution: | |
| suspendability | 80% |

Furthermore the accelerated stability test of the microcapsule suspension has been carried out as described in the characterization, obtaining an IPBC content in the aged formulation of 19.5% and not observing any yellowing phenomenon.

The minimum variation of IPBC content, in combination with the maintenance of the other characteristic values, colour comprised, shows that the microcapsule suspension object of the present invention has substantially maintained unaltered its own starting characteristics, thus resulting stable in the time.

The above mentioned tests are indicative that the so prepared microcapsule suspension is preservable under the environmental conditions for long periods as sediments, mass thickenings, even under tropical conditions (T=54° C.) are not observed.

It has furthermore been observed that, even after exposure for 30 days to light, the microcapsules are white and no yellowing phenomena are observed.

The release test carried out on the suspension maintained at room temperature has given the following values:

| Release at 1': | 0.4% |
|---|---|
| Release at 60': | 7.7% |
| Encapsulation efficiency: | >94% |

These data confirm that the microcapsule wall allows the IPBC outflowing in the time.

From the comparison of the capsule release data of the Example 1 with those of the Example 4, it is noticed that, by changing the process conditions, for example the starting monomers, it is possible to obtain a more or less quick release in the time.

Example 5

204 g of IPBC having a 98% of purity are charged in a vessel equipped with stirrer containing 194 g of Solvesso 200 and 100 g of Agsolex 12 (N-dodecyl pyrrolidone); the mixture thus composed is heated at 50° C. and maintained under stirring until complete homogenisation is obtained. 34.9 g of Voronate M 220 (isocyanate MD1) are then added, always under stirring.

In the meantime 5 g of dispersant Agrimer AL 10 are dispersed in 397 g of water; the above described organic mixture is then added to obtain an oil/water emulsion, by stirring for about 3 minutes with Turrax at the maximum rate (10,000 rpm).

33.5 g of an aqueous solution containing 40% by weight of hexamethylene diamine are then added under stirring by means of a blade stirrer at 800 rpm.

The obtained mixture is transferred into a reactor maintained at 50° C. After few minutes the formulation is completed by addition of 30 g of thickening agent (Rhodopol 23 pregelified at 2.7% by weight in water containing 1 g of Proxel OXL as antimould agent), 2 g of antifoam agent Defomex 1510 and cured for four hours at 50° C.

The suspension of microcapsules thus obtained is characterized as follows:

| IPBC content in the formulation: | 20.1% |
|---|---|
| Particle size: | |
| 50% | <5 micron |
| 90% | <20 micron |
| Viscosity: | 1.700 cPs |
| Stability at dilution: | |
| suspensibility | 80% |
| Accelerated stability test (14 days at 54° C.) | |
| IPBC content | 20.0% |
| Appearance | homogeneous, no yellowing |

The microcapsules suspension object of the present invention, having substantially maintained unaltered its own starting characteristics, with no sediments and mass thickenings, even under tropical conditions (T=54° C.), can be considered perfectly stable with time.

It was furthermore observed that, even after exposure for 30 days to light, no yellowing phenomenon is observed with a resulting whitish colour of microcapsules. The release test performed before ageing in presence of water has given the following values:

| 15 min. | 36% |
|---|---|
| 30 min | 36% |
| 60 min. | 37% |
| 2 h | 40% |
| 4 h | 42% |
| 8 h | 48% |
| Encapsulation efficiency: | >99% |

These data confirm that the microcapsule wall allows the IPBC outflowing in the time.

After suspension ageing the release test was repeated, substantially obtaining unchanged release values:

| Release at 15 min.: | 34% |
|---|---|
| Release at 60 min.: | 35% |

The comparison between the results of example 1 and example 5 concerning the IPBC release in water shows that the presence of N-alkyl pyrrolidone allows to further reduce the release of IPBC from the microcapsules. This slower release rate is an advantage for prolonged use applications.

Example 6

Example 5 has been repeated but replacing Solvesso 200 with Amesolv 4201 (diisopropyl biphenyl isomers mixture $C_{18}H_{22}$).

The mixture thus composed is heated at 50° C. and maintained under stirring until complete homogenization is obtained. 34.9 g of Voronate M 220 (isocyanate MDI) are then added, always under stirring.

In the meantime 5 g of dispersant Agrimer AL 10 are dispersed in 397 g of water; the above described organic mixture is then added to obtain an oil/water emulsion, by stirring for about 3 minutes with Turrax at the maximum rate (10,000 rpm).

33.5 g of an aqueous solution containing 40% by weight of hexamethylene diamine are then added under stirring by means of a blade stirrer at 800 rpm.

The obtained mixture is transferred into a reactor maintained at 50° C. After few minutes the formulation is completed by addition of 30 g of thickening agent (Rhodopol 23 pregelified at 2.7% by weigth in water containing 1 g of Proxel GXL as antimould agent), 2 g of antifoam agent Defomex 1510 and cured for four hours at 60° C.

The suspension of microcapsules thus obtained is characterized as the previous example finding out similar results.

The invention claimed is:

1. Biocidal formulations in aqueous suspension of microcapsules based on 3-iodo-2-propynyl butyl carbamate (IPBC), comprising (parts by weight):
   (1) 10-60 parts of polymeric microcapsules, wherein the microcapsules are water insoluble and obtainable by in situ polymerization by polycondensation, the microcapsule polymer being polyurea, the microcapsules comprising IPBC and a coformulating agent comprising one or more alkylbenzenes, linear or branched having a number of carbon atoms from 9 to 20, the microcapsules showing an IPBC encapsulation efficiency higher than 90%, and the coformulating agent having a boiling point in the range 160° C.-310° C.;
   (2) 1-5 parts of one or more dispersants;
   (3) 1-20 parts of one or more excipients selected from thickeners, antifoam, antifreeze, antimould agents; and
   (4) water to 100,
   wherein the microcapsules have sizes of 1-30 micron.

2. Formulations according to claim 1, wherein the coformulating agent has a distillation range selected from 182°-202° C. or 226°-284° C.

3. Formulations according to claim 1, wherein the dispersant (component (2)) is selected from sodium ligninsulphonates, calcium ligninsulphonates, eta-propo block polymers, sodium polycarboxylates, polyalkenyl pyrrolidone.

4. Formulations according to claim 1, wherein the excipients (3) are as follows: thickeners selected from xanthan rubber; antifoam selected from silicone compounds; antifreeze selected from inorganic salts; preservatives selected from substituted triazines and benzoisothiazolinones.

5. Water-insoluble polyurea microcapsules of the formulation of claim 1 obtained by in situ polymerization by polycondensation, the microcapsules comprising 3-iodo-2-propynyl butyl carbamate (IPBC) and a coformulating agent formed of one or more alkylbenzenes having a number of carbon atoms from 9 to 20, the microcapsules showing an IPBC encapsulation efficiency higher than 90%, and the synergizing agents having a boiling point in the range of 165° C.- 310° C.

6. Formulations of microcapsules according to claim 1, obtained according to the following process:
   a) preparation of a homogeneous IPBC mixture and one or more alkylbenzenes at a temperature in the range of about 15° C. and 70° C., the ratio by weight IPBC/alkyl-benzenes ranging between 1:0.5 and 1:2;
   b) addition to the mixture obtained in a) of one or more water-insoluble monomers, precursors of the polymer forming the microcapsule walls in amounts in the range 5-20% by weight with respect to the weight of the mixture obtained in a);
   c) addition of the organic phase obtained in b) to an aqueous phase comprising at least one dispersant, in a ratio by weight aqueous phase/organic phase between 0.4:1 and 1:1, thus obtaining an oil/water emulsion;
   d) optional addition to the emulsion obtained in c) of the water-soluble monomers, precursors of the polymer forming the microcapsule walls in a molar ratio 0.9-1 with respect to the monomers used in b); and
   e) heating at temperature in the range 50° C.-80° C. to allow the formation of the polymeric membrane forming the microcapsule walls.

7. Formulations according to claim 6, wherein the water insoluble monomers are polymethylene polyphenyl isocyanate (MDI) or MDI mixtures with toluene diisocyanate (TDI).

8. Formulations according to claim 6, wherein the water-soluble monomers to be used in step d) are hexamethylendiamine, optionally in water solution.

9. A process for preparing the formulations of claim 1 comprising the following steps:
   a) preparation of a homogeneous IPBC mixture and one or more alkylbenzenes at a temperature in the range of about 15° C. and 70° C., the ratio by weight IPBC/alkyl-benzenes ranging between 1:0.5 and 1:2;
   b) addition to the mixture obtained in a) of one or more water-insoluble monomers, precursors of the polymer forming the microcapsule walls in amounts in the range 5-20% by weight with respect to the weight of the mixture obtained in a);
   c) addition of the organic phase obtained in b) to an aqueous phase comprising at least one dispersant, in a ratio by weight aqueous phase/organic phase between 0.4:1 and 1:1, thus obtaining an oil/water emulsion;
   d) optional addition to the emulsion obtained in c) of the water-soluble monomers, precursors of the polymer forming the microcapsule walls in a molar ratio 0.9-1 with respect to the monomers used in b); and
   e) heating at temperature in the range 50° C.-80° C. to allow the formation of the polymeric membrane forming the microcapsule walls.

10. A process according to claim 9, the process comprising the following steps:
   a) preparation of a homogeneous IPBC mixture and one or more alkylbenzenes, under stirring, at a temperature in the range 25° C.-70° C., the ratio by weight IPBC/alkylbenzenes ranges between 1:0.5 and 1:2, maintaining under stirring until complete homogenization;
   b) addition to the mixture obtained in a) of one water-insoluble monomer, precursor of the polyurea, in amounts in the range 6-12% by weight with respect to the total weight of the mixture obtained in a), under stirring, maintaining substantially the same temperature of step a);
   c) addition to an aqueous phase comprising at least one dispersant of the organic phase obtained in b), in a ratio by weight aqueous phase/organic phase between 0.6:1 and 0.9:1, under strong stirring by using a high shear rate stirrer, having a speed higher than 5,000 rpm, for at least 3 minutes, thus obtaining an oil/water emulsion;
   d) optional addition to the emulsion obtained in c) of a water-soluble monomer, precursor of the polyurea, optionally in water solution, in a molar ratio 0.9-1 with respect to the isocyanate used in b), under stirring, by using a low shear rate stirrer of the blade type; and e) completion of the polymerization reaction started in d) by maintaining the temperature in the range 50° C.-80° C., for at least three hours.

11. A method of using IPBC as a biocide, comprising the step of contacting a microorganism with the aqueous formulation of claim 1.

12. A method according to claim 11, wherein the aqueous formulation is incorporated into paints, coating products, surfactants, proteins, starch-based compositions, products for cosmetic use, inks, emulsions, resins, plasters, cement surfaces, wood, leathers, plastics, textiles, lubricants, metal working fluids, polymeric dispersions, aqueous based products, latexes containing polyvinyl alcohol, polyacrylates, vinyl polymers, thickening solutions containing cellulose derivatives or kaolin-based suspensions.

13. Formulations in aqueous suspension of microcapsules and microcapsules according to claim 1 wherein the coformulating agent is selected from among biphenyl compounds.

14. Formulations in aqueous suspension of microcapsules according to claim 1, wherein the microcapsules comprise, in addition to IPBC and the coformulating agent, an N-alkyl pyrroldone wherein the alkyl is $C_1$-$C_{18}$.

15. Formulations according to claim 1, wherein the coformulating agent has a distillation range of 220-290° C.

\* \* \* \* \*